United States Patent
Lopez et al.

(10) Patent No.: US 7,238,098 B2
(45) Date of Patent: Jul. 3, 2007

(54) METHOD OF EXTRACTING LIPIDS FROM NACREOUS MOLLUSKS

(75) Inventors: Evelyne Lopez, Paris (FR); Marthe Rousseau, Brest (FR)

(73) Assignee: Robert Wan Holding, Papeete-Tahiti (PF)

( * ) Notice: Subject to any disclaimer, the term of this patent is extended or adjusted under 35 U.S.C. 154(b) by 0 days.

(21) Appl. No.: 10/542,912

(22) PCT Filed: Feb. 3, 2004

(86) PCT No.: PCT/FR2004/000240

§ 371 (c)(1),
(2), (4) Date: Jul. 21, 2005

(87) PCT Pub. No.: WO2004/078156

PCT Pub. Date: Sep. 16, 2004

(65) Prior Publication Data

US 2006/0105689 A1      May 18, 2006

(30) Foreign Application Priority Data

Feb. 4, 2003    (FR) .................................. 03 01246

(51) Int. Cl.
*A22C 29/02* (2006.01)
(52) U.S. Cl. ......................................................... 452/1
(58) Field of Classification Search ..................... None
See application file for complete search history.

(56) References Cited

U.S. PATENT DOCUMENTS 6,682,244 B2 *   1/2004   Gueret ........................ 401/208

FOREIGN PATENT DOCUMENTS

FR         1.350.038         12/1963
FR         2 799 125         4/2001

OTHER PUBLICATIONS

Dunstan et al., "The effect of lyophilization on the solvent extractioin of lipid classes, fatty acids and sterols from the oyster *Crassostrea gigas*" LIPIDS, vol. 28, No. 10, 1993, pp. 937-944. XP0008023254, USA, the whole document.
Patent Abstracts of Japan, vol. 1996, No. 11, Nov. 29, 1996, & JP 8-175950 A (Mikimoto Pharmaceut Co Ltd), Jul. 9, 1996 abstract.
Database WPI, Section Ch, Week 199032, Dewert Publications Ltd. , London, GB; AN 1990-242898, XP002257518 & JP 02-167509 A, (Mikimoto Seiyaku KK), Jun. 29, 1990, abstract.

* cited by examiner

*Primary Examiner*—Thoimas Price
(74) *Attorney, Agent, or Firm*—Birch, Stewart, Kolasch & Birch, LLP

(57) ABSTRACT

The method of extracting a lipidic active principle from a solid material coming from a nacreous mollusk comprises the steps of grinding the nacre into a fine powder, preferably having a mean grain size of less than 20 μm, of putting the powder into contact with a lipid solvent, of separating the solvent, and of extracting the lipidic active principle by evaporating the solvent.

4 Claims, No Drawings

METHOD OF EXTRACTING LIPIDS FROM NACREOUS MOLLUSKS

The present invention relates to a method of extracting an active principle coming from nacreous mollusks, and to a method of extracting the active principle.

BACKGROUND OF THE INVENTION

In order to regenerate the cutaneous barrier of the skin, it is known, in particular from document FR-A-1 350 038, that is it desirable to treat the skin with regenerative cosmetic compositions containing an active principle that is rich in lipids, in particular polar lipids extracted from the flesh of nacreous mollusks, in particular from oyster flesh. The extraction processing is complex since it is necessary to begin by grinding the flesh, either after drying it, or else after dehydrating it. The processing is therefore expensive. In addition, the flesh of nacreous mollusks is suitable for food applications for humans or animals, such that the raw material is itself of non-negligible cost.

OBJECT OF THE INVENTION

An object of the invention is to propose a method enabling an active principle to be extracted from a nacreous mollusk at lower cost.

DETAILED DESCRIPTION OF THE INVENTION

A method is proposed of extracting an active principle coming from nacreous mollusks, the method comprising the steps of separating the nacre from the remainder of the shell of a nacreous mollusk, of grinding the nacre into a fine powder, preferably having mean grain size of less than 20 micrometers ($\mu m$), and more particularly mean grain size of about 8 $\mu m$, of performing lipid extraction on the resulting powder by subjecting it to a lipid solvent, and then of extracting the active principle from the solvent.

Lipid extraction can be performed using any known method such as, for example, subjecting the powder to a lipid solvent such as a mixture of chloroform and methanol, or hot ethanol, and then separating by centrifuging to separate a solid phase from a liquid phase, followed by eliminating the solvent from the liquid phase by evaporation. The resulting active principle is in the form of a brown gel that can be used directly in the cosmetic composition of the invention. In practice, by using nacre powder having a mean grain size of about 8 $\mu m$, about 5 kilograms (kg) of active principle are obtained from one (metric) tonne of nacre. In this context, it should be observed that nacre is a solid that is easy to grind so the processing is inexpensive. In addition, oyster shells constitute waste that is almost worthless, such that the investment for purchasing the raw material can be considered as being zero.

The active principle as obtained in this way is mixed with a conventional cosmetic medium in a proportion of at least 0.2%, and preferably 0.5% to 1% by volume or by weight, depending on the intended application.

Naturally, the invention is not limited to the embodiment described above and can be implemented in various ways without thereby going beyond the ambit of the invention as defined by the claims.

In particular, although provision is made above for nacre to be ground to a mean grain size of about 8 $\mu m$, it is possible to grind less finely, so as to obtain a mean grain size that is preferably less than 20 $\mu m$, with the extracted yield decreasing with coarser grinding.

Although the invention is described as using nacre coming from an oyster of the genus *Pinctada*, species *margaritifera*, it is possible not only to use oysters of a different genus or a different species, but also to use other nacreous mollusks.

It is also possible to proceed with lipid extraction from a mixture of powder coming from the body and from the nacre of the same mollusk or of mollusks that are different from one another, in particular when an analysis of the resulting active principles reveals differences that show it is useful to make a combination.

What is claimed is:

1. A method of extracting a lipidic active principle from a solid material coming from a nacreous mollusk, the method comprising the steps of grinding the nacre into a fine powder, of putting the powder into contact with a lipidic solvent, of separating the solvent, and of extracting the lipid active principle by evaporating the solvent.

2. The method according to claim 1, wherein the nacre is ground to a powder having a mean grain size of less than 20 $\mu m$.

3. The method of extracting lipids according to claim 2, wherein the nacre is ground to a powder having a mean grain size of about 8 $\mu m$.

4. The method according to claim 1, wherein the nacre comes from oysters of the genus *Pinctada* species *margaritifera*.

* * * * *